United States Patent [19]

Nishimura et al.

[11] Patent Number: 5,500,348
[45] Date of Patent: Mar. 19, 1996

[54] BASOPHIL-BINDING MONOCLONAL ANTIBODY, METHOD FOR SEPARATION OF BASOPHILS, METHOD FOR CHEMICAL MEDIATOR RELEASE FROM BASOPHILS, AND METHOD FOR TESTING RELEASE OF BASOPHIL-DERIVED CHEMICAL MEDIATORS

[75] Inventors: Shinji Nishimura, Moriguchi; Hiroshi Nishi, Neyagawa; Masaji Nishimura, Kyoto, all of Japan

[73] Assignee: Shionogi & Co., Ltd., Japan

[21] Appl. No.: 144,447

[22] Filed: Nov. 2, 1993

[30] Foreign Application Priority Data

Nov. 4, 1992 [JP] Japan .................................... 4-321164

[51] Int. Cl.$^6$ ...................... G01N 33/543; G01N 33/577
[52] U.S. Cl. ............................ 435/7.24; 435/2; 436/513; 436/518; 436/526; 436/531; 436/548; 530/388.7
[58] Field of Search ........................... 530/388.2, 388.22, 530/388.7; 435/7.21, 7.8, 177, 180, 70.21, 7.24, 240.27, 2; 436/548, 513, 518, 526, 531

[56] References Cited

U.S. PATENT DOCUMENTS 4,559,310 12/1985 Cantor et al. ........................... 435/7.21

FOREIGN PATENT DOCUMENTS

| 22948/88 | 4/1989 | Australia . |
| 0239400 | 9/1987 | European Pat. Off. . |
| 91/01368 | 2/1991 | WIPO . |

OTHER PUBLICATIONS

MacGlashan et al, 1980, The purification of human basophils, J. Immunol 124:2519–2521.
Valent et al, 1989. Mast cell typing: demonstration of a distinct hematopoietic cell type and evidence for immunophenotypic relationship to mononuclear phagocytes. Blood 73:1778–85.
Van Toorenenberger, 1981. IgG4 and passive sensitization of basophil leukocytes. Int. Archs. Allergy Appl. Immunol 65:432–40.
Lett–Brown et al, 1989. Purification of human basophils. Their response to anti–IgE. J. Immunol. Meth 117:163–7.
Bodger et al, 1987. The purification of human basophils: their immunophenotype and cytochemistry. Br. J. Haematol. 67:281–4.
Schroeder et al, Journal of Immunological Methods, vol. 133, pp. 269–277 (1990).
Gaudernack et al, Journal of Immunological Methods, vol. 90, pp. 179–187 (1986).
Mul et al, Journal of Immunological Methods, vol. 149, pp. 207–214 (1992).
Bodger et al, Blood, vol. 69, No. 5, pp. 1414–1418 (1987).
Valent et al, Int. Arch Allergy Appl. Immunol., vol. 91, pp. 198–203 (1990).
E. F. Knol et al., "Monitoring human basophil activation via CD 63 monoclonal antibody 435", J. Allergy Clin. Immunol, Sep. 1991, vol. 88, pp. 328–338.

Primary Examiner—Toni R. Scheiner
Assistant Examiner—James L. Grun
Attorney, Agent, or Firm—Birch, Stewart, Kolasch & Birch

[57] ABSTRACT

The monoclonal antibodies of the present invention makes it possible to separate basophils suitable for the IgE-mediated specific chemical mediator release test, because it retains its reactivity with basophils even after being immobilized onto a solid carrier, and because it does not inhibit release of chemical mediators induced by allergens or anti-IgE antibody, and does not induce nonspecific release of chemical mediators. Also, the method for separating basophils of the present invention simplifies the separation of basophils from blood, and by using this method, the histamine release test which otherwise requires complex procedures can be simplified. Further, the group of cells obtained by the method for separating basophils of the present invention can easily be utilized in the release tests for chemical mediators released from basophils such as leukotriene and PAF, which otherwise require expertise for handling.

9 Claims, 4 Drawing Sheets

BASOPHIL-BINDING MONOCLONAL ANTIBODY, METHOD FOR SEPARATION OF BASOPHILS, METHOD FOR CHEMICAL MEDIATOR RELEASE FROM BASOPHILS, AND METHOD FOR TESTING RELEASE OF BASOPHIL-DERIVED CHEMICAL MEDIATORS

BACKGROUND OF THE INVENTION

1. Field of the Invention

The present invention relates to monoclonal antibodies, having the properties of (1) being reactive with basophils, (2) retaining their reactivity with basophils even after immobilization onto a solid carrier, (3) not inhibiting IgE-mediated specific histamine release from the basophils, and (4) not inducing nonspecific histamine release from the basophils, and also relates to solid-immobilized monoclonal antibodies which are prepared by immobilizing the monoclonal antibodies onto solid carriers. The present invention further relates to hybridomas producing the monoclonal antibodies, a method for separating basophils from humoral fluids using the monoclonal antibodies, a method for releasing chemical mediators from the basophils separated by the method for separating basophils, and a method for testing release of chemical mediators from basophils.

2. Discussion of the Related Art

The basophil, a kind of leukocyte and a target cell of IgE, stores various chemical mediators such as histamine in granules, and, like mast cells, draws attention as a key entity of allergic reactions.

Generally, there are roughly two mechanisms of chemical mediator release from basophils.

One is such that IgE antibodies bound to receptors on the basophil membrane surface are crosslinked by allergen or anti-IgE antibody and this stimulation causes a degranulation reaction, resulting in chemical mediator release. This corresponds to chemical mediator release by allergic reaction (hereinafter referred to as IgE-mediated specific chemical mediator release). In the other type of chemical mediator release, whose mechanism and significance remain unknown, chemical mediator release occurs directly without crosslinking of the IgEs on the basophil membrane surface. In contrast to the IgE-mediated specific chemical mediator release, this second type of chemical mediator release can occur even in the absence of anti-IgE antibody and allergen (hereinafter referred to as nonspecific chemical mediator release).

In the diagnosis and pathologic analysis of allergic diseases, it is useful to test IgE-mediated specific chemical mediator release, typically by the histamine release test. Histamine, a very important chemical mediator causing type I allergic reactions, is known to induce various reactions such as bronchial smooth muscle constriction and accentuating of vascular permeability. The histamine release test is an unique testing method based on a biological reaction, in which immunoglobulin E (IgE) bound via receptor onto the human peripheral blood basophil surface is reacted with various allergens to release histamine and the amount of histamine thus released is determined. Unlike other methods for allergen identification such as specific IgE tests (e.g., RAST) and skin tests, the histamine release test serves well as a means for searching causative allergens in allergy patients in a setting closer to actual clinical conditions.

This histamine release test using peripheral blood can be carried out in two different ways, one using whole blood and the other using washed leukocytes. Although the whole blood method may be useful in generally determining the patient's allergic condition, there is the possibility that non-basophil serum components can affect histamine release assay. For this reason, it is common practice to use washed leukocytes when accurate basophil reactivity is analyzed for research into the mechanism of action of drugs etc. or for basic research into the mechanism of histamine release. However, separation of washed leukocytes requires troublesome procedures, including erythrocyte removal with dextran solution, followed by two or three cycles of centrifugation and washing and subsequent leukocyte count adjustment. This results in a requirement for an increased volume of blood for the test. These drawbacks pose many problems for use of the washed leukocyte method as a routine testing method.

It is also known that substances released upon basophil degranulation include chemical mediators which have potent vascular permeability accentuating activity/leukocyte migrating capability, such as leukotriene and platelet activating factor (PAF). These various chemical mediators from basophils are now being basically studied for pathologic analysis of allergy. However, most of these chemical mediators are rapidly metabolized after release into the blood, and it is a key to successful assay thereof to handle the sample in a quick and strictly controlled manner. At present, it is very difficult to analyze most of such chemical mediators from basophils.

As stated above, chemical mediator release from basophils involves two types: IgE-mediated specific chemical mediator release by allergic reaction and nonspecific chemical mediator release. In the diagnosis of allergic diseases, it is necessary to test the IgE-mediated specific chemical mediator release. However, troublesome operation and a large amount of blood are required because leukocytes must be separated to ensure the histamine release test without influence of serum components as described above. This is undesirable for routine examination. In addition, it is also difficult to analyze chemical mediators other than histamine because of troublesome handling of the samples.

In this situation, the present inventors investigated in order to solve the above problem by separating basophils from the blood and using them in release tests for histamine etc.

Conventional methods for basophil separation/purification include the method of Frederik P. J. Mul et al (Journal of Immunological Methods 149, 207 (1992)), in which impurity cells are removed from the sample, the basophil density of which is previously increased by gravitational centrifugation, using magnetic particles coupled with an antibody reactive to non-basophil cell components, to purify basophils.

However, this method is not intended to separate the desired basophil itself but intended to remove impurities, and its efficiency is poor and operation is troublesome.

On the other hand, there are a large number of antibodies known to be reactive to the basophil itself (e.g., P. Valent et al., International Archives Allergy Applied Immunology 91, 198 (1990) and M. P. Bodger et al., Blood 69, 1414 (1987)).

However, there have been no successful attempts of immobilizing such a basophil-reactive antibody to a solid carrier and using it to separate human basophils. Accordingly, there have been no attempts to use thus-separated human basophils in a release test for chemical mediators such as histamine.

Although this fact may be attributable to failures due to loss of reactivity of the antibody with basophils as a result of immobilizing of the basophil-reactive antibody onto the solid carrier (Experimental Example 1 (1) below), it is most likely that the basophils separated by means of such a basophil-reactive antibody have been damaged so that IgE-mediated specific histamine release of the basophils is inhibited (e.g., Frederik P. J. Mul et al., Journal of Immunological Methods 149, 207 (1992) and J. T. Schroeder et al., Journal of Immunological Methods 133, 269–277 (1990)) and their nonspecific histamine release is markedly induced, and therefore the basophils cannot be used for histamine release reaction assay etc. (Experimental Example 1 (2) below). It can be assumed that Frederik et al. employed their apparently roundabout method, in which basophils are purified using an antibody reactive to non-basophil cell components, to avoid the above drawback.

However, provided that basophils can be separated and purified using a basophil-reactive antibody which specifically targets basophils, a simple and very precise purification will be possible.

SUMMARY OF THE INVENTION

With the above in mind, the present inventors investigated in search for an antibody which can be used for this purpose, i.e., a monoclonal antibody which retains its reactivity with the basophil even after immobilization on a solid carrier and which does not damage the basophil even after coupling with the basophil, i.e., a monoclonal antibody which does not have significant influence on IgE-mediated specific histamine release from the basophil or on nonspecific histamine release from the basophil. As a result, the inventors have succeeded in preparing the desired monoclonal antibody. The inventors established a method for easily separating basophils by immobilizing such an antibody onto a solid carrier, reacting it with a humoral fluid, capturing basophils in the humoral fluid with the monoclonal antibody and then removing the unreacted humoral fluid, and succeeded in reacting the separated basophils with an allergen or an anti-IgE antibody to release histamine. Also, the present inventors have established a method for testing IgE-mediated specific histamine release from basophils which were separated using said antibody, and completed the present invention.

Accordingly, an object of this invention is to provide monoclonal antibodies overcoming the above-noted drawbacks.

Another object of this invention is to provide a solid carrier-immobilized monoclonal antibody which is prepared by immobilizing the monoclonal antibody of the present invention onto a solid carrier.

A further object of this invention is to provide a hybridoma which produces the monoclonal antibody of the present invention.

Yet another object of this invention is to provide a method for separating basophils from humoral fluids using the solid carrier-immobilized monoclonal antibody.

A still further object of this invention is to provide a method for releasing a chemical mediator from basophils using the separated basophil.

An additional object of this invention is to provide a method for testing chemical mediator release from basophils.

The monoclonal antibodies of the present invention have the following properties:

(1) Being reactive with basophils, (2) Retaining their reactivity with basophils even after immobilization onto a solid carrier, (3) Not inhibiting IgE-mediated specific histamine release from the basophils, and (4) Not inducing nonspecific histamine release from the basophils.

The monoclonal antibodies of the present invention makes it possible to separate basophils suitable for the IgE-mediated specific chemical mediator release test, because they retain their reactivity with basophils even after being immobilized onto a solid carrier, and because they do not inhibit IgE-mediated specific chemical mediator release from basophils caused by allergens or anti-IgE antibody, and do not induce nonspecific chemical mediator release from basophils. Also, the method for separating basophils of the present invention simplifies the separation of basophils from blood, and by using this method, the histamine release test which otherwise requires complex procedures can be simplified. Further, the cells obtained by the method for separating basophils of the present invention can easily be utilized in the release tests for chemical mediators released from basophils such as leukotriene and PAF. In the absence of the present method, expert handling is required to obtain cells adequate for testing leukotriene or PAF release.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein.

DETAILED DESCRIPTION OF THE INVENTION

The present invention relates to monoclonal antibodies having the following properties:

(1) Being reactive with basophils, (2) Retaining their reactivity with basophils even after immobilization onto a solid carrier, (3) Not inhibiting IgE-mediated specific histamine release from the basophils, and (4) Not inducing nonspecific histamine release from the basophils.

With respect to the monoclonal antibody provided by the present invention, which has the above-described properties (1), (2), (3) and (4), "(1) Being reactive with basophils" means that the monoclonal antibody reacts with a basophil surface antigen.

Also, "(2) Retaining their reactivity with basophils even after immobilization onto a solid carrier" means that the monoclonal antibody does not lose its basophil-capturing capability even after the immobilization on a solid carrier. Any carrier can be used for this purpose, as long as it is an ordinary carrier for solid immobilization of antibody, such as glass or synthetic resin particles (beads), spheres (balls), tubes, plates or magnetic particles such as magnetic beads, with a preference given to magnetic particles.

The basophil-capturing capability of a solid carrier-immobilized antibody is determined by testing whether it can couple with basophils or not. Specifically, this determination is carried out by the method described below, using histamine as an index. First, a monoclonal antibody reactive with the human basophil, immobilized on magnetic beads, is made to react with human blood. Next, the beads are collected with a magnet and the supernatant is removed, after which a histamine release buffer (the HEPES buffer containing calcium chloride, magnesium chloride, etc.) is added, and freeze-thawing is repeated in several cycles. The total histamine content in the supernatant is determined by a known method such as a histamine assay system using HPLC (Y. Tsuruta et al., Journal of Chromatography 224, 105 (1981)) (manufactured by Shimadzu Corporation. An antibody for which histamine is detected is selected as an antibody having basophil capturing capability.

Also, "(3) Not inhibiting IgE-mediated specific histamine release from the basophils" means that the basophil coupled with the monoclonal antibody substantially maintains its IgE-mediated specific histamine release capability which is naturally observed in the blood.

Whether or not the basophil substantially maintains its IgE-mediated specific histamine release capability can be confirmed by a comparative experiment with BA312, a monoclonal antibody found in the present invention.

Specifically, since the basophil captured by BA312 maintains its histamine release capability which is naturally observed in the blood (Experimental Example 2 below), the subject solid-immobilized monoclonal antibody is judged as "not inhibiting IgE-mediated specific histamine release from the basophils" and as "being within the scope of the present invention," when the amount of histamine released from the basophils coupled with the subject monoclonal antibody is not less than 60% of that released from the basophils coupled with BA312 as determined by reacting the subject solid carrier-immobilized monoclonal antibody with basophils under the same conditions as those for solid carrier-immobilized BA312, and treating the resulting two samples of basophils coupled with respective monoclonal antibodies with anti-IgE antibody under the same conditions to release histamine.

Also, "(4) Not inducing nonspecific histamine release from the basophils" means that the amount of nonspecific histamine release from the basophils coupled with the monoclonal antibody is not more than 30% of the amount of IgE-mediated specific histamine release.

The amount of nonspecific histamine release can be determined by adding to the basophils an appropriate solvent such as a hydroxyethylpiperazine-N'-2-ethanesulfonic acid (HEPES) buffer containing calcium chloride, magnesium chloride, human serum albumin (HSA), etc. (hereinafter referred to as histamine release buffer), carrying out a reaction at 10° to 50° C. for 10 to 60 minutes to release histamine, and then measuring the released amount of histamine using a known method such as HPLC.

The amount of IgE-mediated specific histamine release can be determined by reacting the basophils with the anti-IgE antibody dissolved in the histamine release buffer at the same reaction temperature and for the same reaction time as above, and measuring the amount of histamine released by the same method and under the same conditions as above.

A method for preparing the monoclonal antibody of the present invention is hereinafter described briefly.

1) Preparation of hybridomas

A mouse is immunized with human basophils by several intraperitoneal, subcutaneous or intravenous injections of human basophils at intervals of several weeks. Antibody-producing cells are collected from the immunized mouse and fused with myeloma cells to yield hybridomas. The thus-obtained hybridomas are tested for human basophil reactivity, and a hybridoma which produces an antibody reactive with human basophils are selected as positive hybridomas.

The thus-selected hybridoma is cloned. After the antibody produced by the resulting hybridoma clone is immobilized onto magnetic beads, said beads being previously coupled with sheep anti-mouse immunoglobulin antibody, the human blood basophil-capturing capability of the antibody and the histamine release properties of the separated basophils are determined.

The basophil-capturing capability can be determined by the method described above.

For determining the histamine release property of the separated basophils, the antibody immobilized on magnetic beads is made to react with human blood as described in the determination of the basophil-capturing capability. The beads are collected with a magnet, and the supernatant is removed, after which the amounts of nonspecific histamine release and those of IgE-mediated specific histamine release of the cells bound to the beads are determined by the method described above. The antibody which has not inhibited IgE-mediated specific histamine release and which has not induced nonspecific histamine release, i.e., the antibody, with which the amount of nonspecific histamine release is not more than 30%, preferably not more than 10% of IgE-mediated specific histamine release, is selected.

Thus, a hybridoma clone producing an antibody which retains its reactivity with its basophils, that is, basophil-capturing capability, even after immobilization on a carrier, which does not inhibit IgE-mediated specific histamine release from the separated basophils, and which does not induce nonspecific histamine release from the separated basophils is selected. This hybridoma clone is cultured, and the monoclonal antibody is recovered.

The above-described immunization, cell fusion, selection of fused cell, cloning, etc. can be carried out by known ordinary methods.

2) Preparation of monoclonal antibody

The selected hybridoma is proliferated by in vitro culture or in vivo culture to yield a monoclonal antibody. In the in vitro culture method, the hybridoma is cultured in an RPMI medium supplemented with fetal calf serum (complete RPMI medium) until the proliferation limit is reached, and the culture supernatant is recovered to obtain the monoclonal antibody. In the in vivo culture method, the hybridoma is transferred to the abdominal cavity of a mouse, previously treated by intraperitoneal administration of pristane, and several weeks later abdominal swelling is confirmed and ascites fluid is collected. From the ascites fluid, an IgG or IgM fraction is separated and purified by an appropriate combination of known methods such as ammonium sulfate fractionation and DEAE-Sepharose column chromatography to obtain the desired monoclonal antibody.

The hybridomas obtained by the above method which produce the monoclonal antibodies of the present invention, BA101, BA20, BA135 or BA312, have been deposited since Sep. 10, 1992 with the Fermentation Research Institute, Agency of Industrial Science and Technology, 1–3, Higashi 1-chome, Tsukuba-shi, Ibaragi-ken 305, Japan, under the terms of the Budapest Treaty as "BA101 SHIONOGI," "BA20 SHIONOGI," "BA135 SHIONOGI," and "BA312 SHIONOGI," under accession numbers of FERM BP-4004, FERM BP-4005, FERM BP-4006 and FERM BP-4007, respectively.

The monoclonal antibody of the present invention is thus exemplified by those produced by the deposited hybridomas. However, any monoclonal antibody is within the scope of the present invention as long as it has the above-described properties of (1) to (4), with a preference given to monoclonal antibody BA312.

The monoclonal antibody of the present invention reacts with leukocytes, including the human basophil, but does not react with human erythrocytes. The monoclonal antibody of the present invention is capable of satisfactorily capturing basophils even after immobilization onto a solid carrier, and does not induce nonspecific chemical mediator release from the captured basophil nor inhibit IgE-mediated specific chemical mediator release. Also, the monoclonal antibody of the present invention can be advantageously used as a solid carrier-immobilized monoclonal antibody obtained by immobilizing it onto a carrier as described above. The method for immobilizing the monoclonal antibody onto a solid carrier is not subject to limitation, and can be carried out by a known method such as the method of Lea et al. (T. Lea et al., Scandinavian Journal of Immunology 22, 207 (1985)). For example, the monoclonal antibody is reacted with a solid carrier, which is uncoated or coated with a compound having a functional group such as a tosyl group or with anti-mouse immunoglobulin, at 0° to 50° C., preferably 4 to 40° C. for 5 minutes to 72 hours, preferably 30 minutes to 48 hours.

The present invention also provides a basophil separation method wherein the solid carrier-immobilized monoclonal antibody of the present invention as obtained above is made to react with a humoral fluid and basophils in the humoral fluid are captured by coupling to the solid carrier-immobilized monoclonal antibody.

Such humoral fluids include blood, nasal secretions, tears and saliva, with a preference given to blood.

There are various widely known methods for coupling an antibody to magnetic particles and separating the desired type of cells, including the method reported by Gaudernack et al. (G. Gaudernack et al., Journal of Immunological Methods 90, 179 (1986)). Another method was reported by Mul et al., in which impurity cells other than basophils are removed from the sample whose basophil density has been previously increased by gravitational centrifugation, using magnetic particles coupled with an antibody reactive to non-basophil cell components, to purify basophils (Mul et al., Journal of Immunological Methods 149, 207 (1992)). However, this method is essentially different from the present invention in that an antibody against the basophil is used in the present invention while an antibody against a non-basophil cell is used in the method of Mul et al.

On the other hand, the basophil separation method of the present invention permits separation of a basophil-rich cell sample by a simple procedure in which the monoclonal antibody of the present invention is immobilized onto a solid carrier such as a magnetic particle directly or via anti-mouse immunoglobulin to yield an antibody-coupled magnetic particle, which is then reacted with a humoral fluid, preferably blood, at 0° to 50° C., preferably 15 to 40° C. for a short period of time (1 to 60 minutes), after which the magnetic particle is collected with a magnet to collect basophils from the unreacted sample.

The present invention also provides a method for testing chemical mediator release from basophils wherein basophils separated by the basophil separation method of the present invention are made to react with allergen or anti-IgE antibody.

Any allergen commonly used in the diagnosis of allergy can be used according to necessity, which includes inhalants such as house dust and pollen, dietary allergens such as meat and eggs, and chemical substances.

The reaction of the basophils with an allergen or anti-IgE antibody is carried out at 10° to 50° C., preferably 25° to 40° C. for 0.5 to 300 minutes, preferably 10 to 60 minutes.

The present invention also provides a method for testing chemical mediator release from basophils comprising the following steps (a) through (c):

Step (a): reacting the solid carrier-immobilized monoclonal antibody of the present invention with humoral fluid and capturing basophils in the humoral fluid by coupling the basophils with the solid carrier-immobilized monoclonal antibody to separate basophils;

Step (b): reacting the basophils separated in the step (a) with allergen or anti-IgE antibody to release a chemical mediator from the basophils; and Step (c): determining the amount of the chemical mediator released from the basophil in the step (b).

It is preferable that steps (a) and (b) described above be carried out in accordance with the above-described basophil separation method of the present invention and the method for chemical mediator release from basophils described above.

The determination of the amount of released chemical mediator in step (c) can be achieved by a known method chosen as appropriate for the desired chemical mediator. For example, in the case of histamine, the amount can be determined by a histamine assay system using HPLC (Y. Tsuruta et al., Journal of Chromatography 224, 105 (1981)) (Shimadzu Corporation). In the case of leukotriene and PAF, the amount can be determined by the method of Hayes et al. (E. Hayes et al., Journal of Immunology 131, 429 (1983)) and the method of Smal et al. (M. A. Smal et al., Journal of Immunological Methods 128, 183 (1990)), respectively. Specifically, the histamine assay using HPLC can be performed in the following steps: a sample is passed through a column packed with a cation exchange resin to elute histamine; 0.1% orthophthalaldehyde and NaOH are added to the eluate and allowed to react with histamine at 45° to form a histamine phosphor; the histamine phosphor is made to react with $H_2SO_4$ for stabilization and intensification of fluorescence; and then the intensity of fluorescence is determined. The amount of chemical mediators can be determined by RIA. In the case of leukotriene assay using RIA, it can be performed as follows: anti-leukotriene antibody and $^3$H-labeled leukotriene are added to a sample or a standard non-labeled leukotriene and allowed to react at 4° C. for 5 to 24 hours; the obtained mixture is made to react with dextran-coated charcoal for 10 minutes while cooling in ice; and then the resulting mixture is centrifuged and the radioactivity of the supernatant is determined. In the case of PAF assay using RIA, it can be performed as follows: anti-PAF antibody, $^{125}$I-labeled PAF and the second antibody are added to a sample or a standard non-labeled PAF and allowed to react for 5 to 24 hours; the obtained mixture is centrifuged, and the radioactivity of the sediment is determined. In the case of histamine assay by RIA, a sample or a standard non-labeled histamine is made to react with anti-histamine antibody and $^{125}$I-labeled histamine at 0° to 40° C., preferably at 0° to 10° C., for 5 minutes to 48 hours, preferably for 30 minutes to 24 hours. Then a B/F separating agent such as polyethyleneglycol is added and allowed to react for 10 minutes while cooling in ice. After centrifugation, the radioactivity of the sediment is determined. The amount of histamine can also be determined by EIA. Although any known EIA methods such as the sandwich method, competitive method and ELISA can be used, a preference is given to the method reported, for example, by Knox Van Dyke, et al. (Luminescence Immunoassay and Molecular Application, CRC Press, pp.2–10, (1990)). Specifically, a mixture of a sample, biotin-labeled standard histamine and enzyme-labeled anti-histamine antibody is made to react with an avidin-immobilized carrier. After washing, the enzymatic activity of the complex between biotin-labeled histamine and enzyme-labeled anti-histamine antibody, which is bound with the avidin-immobilized carrier, is determined. Any carriers and enzymes that are usually used for EIA can be used, but it is preferable to use a microplate as the carrier and a horseradish peroxidase as the enzyme.

In the testing method of the present invention, it is preferable to simultaneously determine the total amount of chemical mediators (in accordance with the method for determining the total amount of histamine) and the amount of nonspecific chemical mediator release in accordance with the method described above, and calculate the ratio of the IgE-mediated specific chemical mediator release using the following equation in order to cancel the influence of nonspecific chemical mediator release from the separated basophils:

Ratio of specific chemical mediator release (%) =

$$\frac{\begin{array}{c}\text{Amount of chemical}\\\text{mediator released by}\\\text{IgE specific reaction}\end{array} - \begin{array}{c}\text{Amount of chemical}\\\text{mediator released by}\\\text{nonspecific reaction}\end{array}}{\text{Total amount of chemical mediator} - \begin{array}{c}\text{Amount of chemical}\\\text{mediator released by}\\\text{nonspecific reaction}\end{array}} \times 100$$

EXAMPLES

The present invention is hereinafter described in more details by means of the following working examples, but the present invention is not limited by them.

1. Preparation of Basophil-Reactive Monoclonal Antibody (1) Immunization

To 2 female BALB/c mice at 8 weeks of age, 1×10$^6$ human basophils per mouse were intraperitoneally administered, followed by intraperitoneal administration of 1×10$^6$ human basophils three times at 3-week intervals.

(2) Cell fusion

Three days after the final immunization, the spleen was excised from each mouse and prepared as a cell suspension in RPMI medium. These splenocytes (2×10$^8$) and NS-1 myeloma cells (6×10$^7$) were mixed and centrifugally settled. To the sediment, 1 ml of 50% polyethylene glycol (average molecular weight of 4000) was added with gentle stirring, followed by stirring for 1 more minute. To this mixture, 1 ml of RPMI medium was added over a 1-minute period, followed by addition of 1 ml and then addition of 7 ml over a 3-minute period. After centrifugal sedimentation, the sediment was suspended in 40 ml of an RPMI medium containing 15% fetal calf serum (complete RPMI medium), and this suspension was inoculated to four 96-well microplates at 0.1 ml per well, followed by cultivation at 37° C. in the presence of 7% carbon dioxide. Twenty-four hours later, 0.1 ml of a complete RPMI medium containing 100 μM hypoxanthine, 0.4 μM aminopterin and 16 μM thymidine (HAT medium) was added. At 2, 3, 5 and 8 days of cultivation, 0.1 ml of the culture supernatant was discarded, and 0.1 ml of HAT medium was added. At 11 and 14 days, 0.1 ml of the culture supernatant was discarded, and 0.1 ml of a complete RPMI medium containing 100 μM hypoxanthine and 16 μM thymidine (HT medium) was added. From all the 384 wells, hybridoma colonies appeared.

(3) Selection of hybridomas

Hybridomas in each culture plate well were cultured in a complete RPMI medium, and the culture supernatant was assayed for specific antibody production as follows:

To 20 ml of human peripheral blood, 5 ml of a physiological saline containing 5% dextran was added to precipitate erythrocytes, after which leukocytes were separated from the supernatant. From these leukocytes, cells having a specific gravity ranging from 1.07 to 1.08 were separated by the discontinuous gravitational centrifugation method using two Percoll solutions prepared at specific gravities of 1.07 and 1.08. The separated cells were stained by the Alcian Blue method (S. G. Harriet et al., Blood 46, 279 (1975)), and basophils were counted. A cell suspension was prepared at 4×10$^5$ basophils/ml in a 10 mM hydroxyethylpiperazine-N'-2-ethanesulfonic acid (HEPES) buffer (pH 7.4) containing 0.8% sodium chloride, 0.037% potassium chloride and 0.03% human serum albumin (HSA) (HA-HEPES buffer). The suspension was dispensed to test tubes at 2×10$^4$ basophils per test tube. 50 μl of the hybridoma culture supernatant was added to each test tube, followed by reaction at 37° C. for 1 hour. After the reaction mixture was once washed with HA-HEPES buffer, a 50 μl mixture of goat anti-human IgE antibody labeled with fluorescein isothiocyanate (FITC) and goat anti-mouse immunoglobulin antibody labeled with phycoerythrin was added, followed by reaction at room temperature for 1 hour. After being once washed with HA-HEPES buffer, the reaction mixture was observed under a fluorescent microscope to determine whether the FITC-labeled cells were labeled by phycoerythrin as well. Thus, one hundred wells, in which the monoclonal antibody contained in the hybridoma culture supernatant was reactive to the FITC-labeled basophil, were selected.

After the thus-selected hybridomas were cloned by the limiting dilution method, each clone was cultured in a flask until the proliferation limit was reached. A 1 ml portion of this culture supernatant was added to 15 mg of magnetic beads, previously coupled with sheep anti-mouse immunoglobulin antibody, followed by reaction at 4° C. for 16 hours with gentle stirring, to yield magnetic beads having a monoclonal antibody immobilized thereon. Using these magnetic beads, human peripheral blood basophil capturing capability and the IgE-mediated specific histamine release and nonspecific histamine release properties of the separated basophils were examined in accordance with the method described in Example 4 below. As a result, hybridomas BA101 Shionogi (FERM BP-4004), BA20 Shionogi (FERM BP-4005), BA135 Shionogi (FERM BP-4006) and BA312 Shionogi (FERM BP-4007) were selected, which respectively produce monoclonal antibodies BA101, BA20, BA135 and BA312, which possess the above-described properties and which are suitable to the methods of the present invention for separation of cells including the human basophils and for testing of histamine release from the separated cells, as demonstrated in Experimental Example below.

The above four kinds of monoclonal antibodies were identified as to mouse immunoglobulin class. It was shown that BA20, BA101 and BA135 belong to class IgG1, while BA312 belongs to class IgM.

(4) Preparation of monoclonal antibody (a) In vitro culture

The hybridoma was cultured in a complete RPMI medium until the proliferation limit ($1\times10^6$ cells/ml) was reached, and the culture supernatant was recovered.

(b) In vivo culture

To a BALB/c mouse, previously treated with intraperitoneal administration of 0.5 ml of pristane, $5\times10^6$ hybridomas were intraperitoneally transplanted. About 3 weeks later, abdominal swelling was confirmed, and abdominal ascites were collected.

(5) Purification of monoclonal antibodies (a) Protein A affinity chromatography

The abdominal ascites obtained in the above process were salted out with an 18% sodium sulfate solution, and the resulting precipitate was dissolved in 0.01M borate-buffered saline (pH 8.0), followed by dialysis against the same solution. A 20 mg aliquot of the monoclonal antibody obtained by this salting-out was dissolved in 2 ml of 0.01 M borate-buffered saline (pH 8.0) and adsorbed to a column (1.6×5 cm) of protein A-Sepharose (manufactured by Pharmacia AB). After impurities were washed out with about 50 ml of 0.01M borate-buffered saline (pH 8.0), the column was eluted with about 100 ml of 0.01M citrate-buffered saline (pH 4.0) to yield purified monoclonal antibodies BA20, BA101 and BA135.

(b) Sepharose CL-4B gel chromatography

A 20 mg aliquot of each monoclonal antibody obtained by the above salting-out process was dissolved in 2 ml of 0.01M borate-buffered saline and fractionated through a column (1.6×70 cm) of Sepharose CL-4B (manufactured by Pharmacia AB). The fraction of the main peak was collected to obtain a purified monoclonal antibody BA312.

2. Solid Immobilization of Monoclonal Antibody on Beads Coupled with Secondary Antibody A 30 mg beads/ml suspension of Dynabeads M-450 sheep anti-mouse immunoglobulin (manufactured by Dynal) was stirred and then dispensed to a 1 ml test tube. After the beads were collected with a magnet and the supernatant was removed, 1 ml of the hybridoma culture supernatant was added, followed by reaction at 4° C. for 16 hours with gentle stirring. After the beads were collected with a magnet and the supernatant was removed, the beads were washed 4 times with HA-HEPES buffer at 4° C. for 30 minutes at a time with gentle stirring, to yield magnetic beads having a monoclonal antibody immobilized thereon.

Other magnetic beads having a monoclonal antibody immobilized thereon were prepared in the same manner as above except that the hybridoma culture supernatant was replaced by 1 ml of a purified monoclonal antibody (20 µg/ml) prepared with HA-HEPES buffer.

3. Immobilization of Monoclonal Antibody on Uncoated Beads

A 30 mg beads/ml suspension of Dynabeads M-450 Uncoated (manufactured by Dynal) was stirred and then dispensed to a 1 ml test tube. After the beads were collected with a magnet and the supernatant was removed, a 1 ml solution of BA312 (0.3 mg/ml) in 0.05 M Tris-HCl buffer (pH 9.5) was added, followed by vigorous stirring. While giving gentle stirring, a reaction was carried out at 4° C. for 16 hours. After the beads were collected with a magnet and the supernatant was removed, the beads were washed 4 times with 0.01M HEPES buffer (pH 7.4) containing 0.5% HSA for 5 minutes at a time, and then washed with HA-HEPES buffer at 4° C. for 16 hours, to obtain magnetic beads having BA312 immobilized thereon.

4. Cell separation and histamine release reaction using magnetic beads having an monoclonal antibody immobilized thereon To 10 ml of normal human blood collected in an EDTA blood sampling tube, 40 ml of HA-HEPES buffer was added to prepare a 20% blood solution. A suspension of magnetic beads having the monoclonal antibody in the culture supernatant of hybridoma BA20 Shionogi, BA101 Shionogi, BA135 Shionogi or BA312 Shionogi immobilized thereon were prepared at 3 mg beads/ml with HA-HEPES buffer. The 20% blood solution was dispensed to test tubes at 500 µl per test tube. To each test tube, 50 µl of the above-described suspension of magnetic beads having BA20, BA101, BA135 or BA312 immobilized thereon were added, followed by reaction at room temperature for 5 minutes with gentle shaking. After the beads were collected with a magnet and the supernatant was removed, the beads were once washed with 500 µl of HA-HEPES buffer. After completion of the washing, 500 µl of a 20 mM HEPES buffer (pH 7.0) containing 0.5 mM calcium chloride, 0.25 mM magnesium chloride, 0.1% glucose, 0.9% sodium chloride, 0.035% sodium bicarbonate and 0.1% HSA (histamine release buffer) or 500 µl of a 4 µg/ml suspension of monoclonal anti-human IgE antibody (HE-69B) in histamine release buffer was added, followed by stirring to give a sample. The total histamine content in the separated cells in the sample was determined using the sample after 3 cycles of freeze-thawing in the histamine release buffer. The IgE-mediated specific histamine release reaction was carried out by reacting the sample with monoclonal anti-human IgE antibody at 37° C. for 1 hour. The nonspecific histamine release reaction was carried out by incubating the sample in the histamine release buffer at 37° C. for 1 hour. After completion of the reaction, the reaction mixture was stirred and then centrifuged at 1500 rpm for 5 minutes, and 300 µl of the supernatant was obtained. The amount of histamine released was determined by a histamine assay system with HPLC (Y. Tsuruta et al., Journal of Chromatography 224, 105 (1981)) (manufactured by Shimadzu Corporation).

Figure 1:
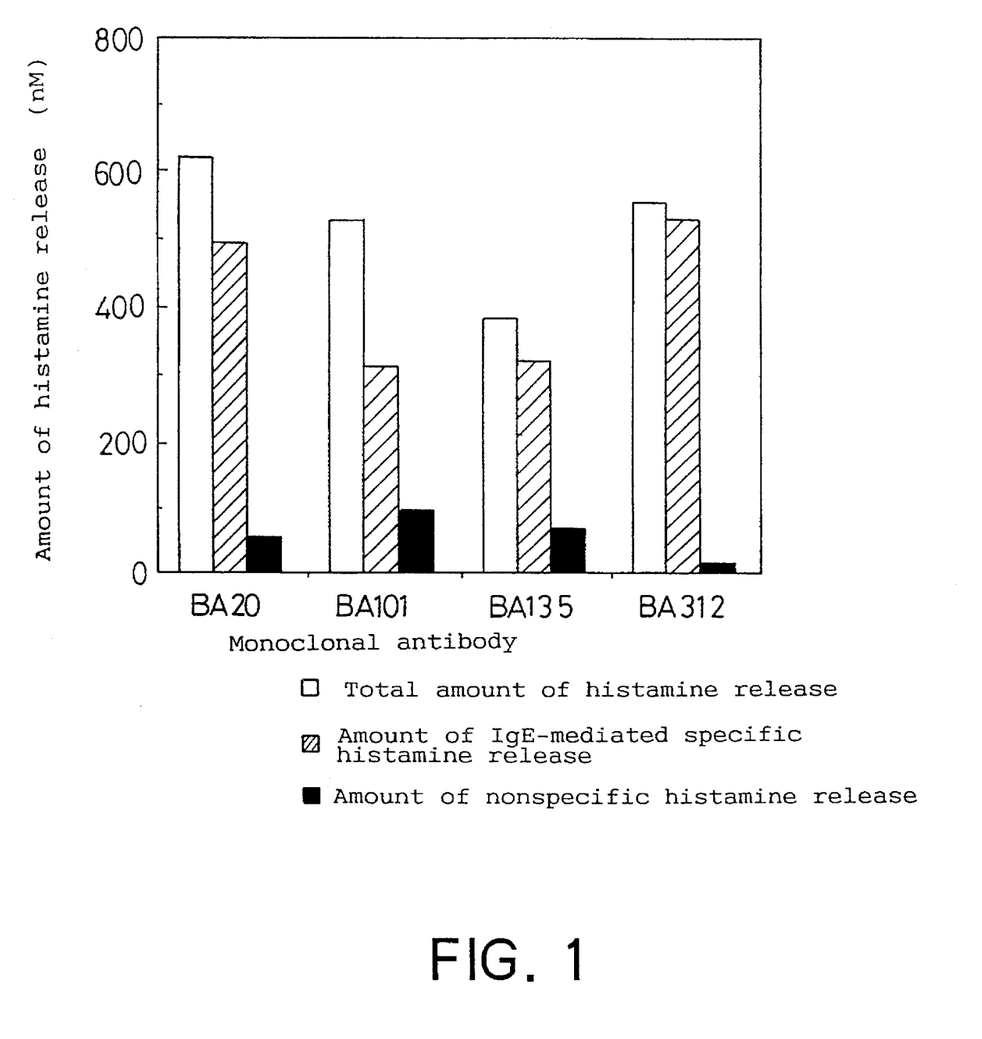
FIG. 1 is a graph showing the total amount of histamine in the basophils separated with the monoclonal antibody of the present invention immobolized on beads (white bar), the amount of IgE-mediated specific histamine release from the basophils (hatched bar), and the amount of nonspecific histamine release from the basophils (black bar).

As shown in Table 1, when determination was made of the total histamine content in the cells separated with magnetic beads having BA20, BA101, BA135 or BA312 immobilized thereon, histamine was detected for all the antibodies, demonstrating basophil separating capability. Also, as shown in FIG. 1, the separated cells showed a good ratio of IgE-mediated specific histamine release, and the nonspecific histamine release was suppressed below 30% of the specific histamine release.

TABLE 1

|  | BA20 | BA101 | BA135 | BA312 | Beads without antibody |
|---|---|---|---|---|---|
| Blood sample | ++ | ++ | ++ | ++ | − |

Basophil separating capability: ++ present, − absent

Experimental Example

1. Comparison of CD Antibodies with Monoclonal Antibodies of the Present Invention (1) Basophil-capturing capability Using CD antibodies reactive to antigens showing good expression on the basophil surface, i.e., CD9 antibody (TP82™, manufactured by Nichirei), CD11b antibody (BEAR1™, manufactured by Immunotech), CD13 antibody (MCS2™, manufactured by Nichirei) and CD32 antibody (2EI™, manufactured by Immunotech), as reported by Valent et al. (P. Valent et al., International Archives Allergy Applied Immunology 91, 198 (1990)), magnetic beads having each antibody immobilized thereon were prepared by the method described in Example 2 above. Using magnetic beads having one of the above CD antibodies, BA20 or BA312 immobilized thereon, a particular group of cells were separated from blood sample A and B and the total amount of histamine derived from the separated cells was determined in the same manner as in Example 4.

As shown in Table 2, CD9 antibody, CD11b antibody, BA20 and BA312 showed good basophil-capturing capability, while CD13 antibody and CD32 antibody did not.

TABLE 2

|  | CD9 | CD11b | CD13 | CD32 | BA20 | BA312 |
|---|---|---|---|---|---|---|
| Blood sample A | ++ | ++ | − | − | ++ | ++ |
| Blood sample B | ++ | ++ | − | − | ++ | ++ |

Basophil-capturing capability: ++ present, − absent (2) Histamine release capability of separated cells Of the CD antibodies examined in Experimental Example 1 (1) above, those showing basophil-capturing capability, namely CD9 antibody and CD11b antibody, and BA20 and BA312 were each immobilized onto magnetic beads. Cells separated using these magnetic beads were evaluated for three parameters of histamine release capability, i.e., the total amount of histamine, the amount of IgE-mediated specific histamine release and the amount of nonspecific histamine release. These tests were performed in the same manner as in Example 4 above, using 20 normal human blood samples.

As a result, all antibodies proved to have basophil capturing capability, and although there were sample-to-sample differences, IgE-mediated specific histamine release was demonstrated for all the antibodies.

In the present invention, an antibody immobilized on magnetic beads is assumed to be useful in chemical mediator release tests, provided that the relative amount of nonspecific histamine release is not higher than 30%, particularly not higher than 10%, of the amount of IgE-mediated specific histamine release from the basophils captured and separated by the antibody. In the case of CD9 antibody and CD11b antibody, the cells captured and separated by these antibodies often show markedly higher nonspecific histamine release in comparison with IgE-mediated specific histamine release; therefore, the above ratio by far exceeds 30%, as shown in Table 3, and it was very difficult to analyze IgE-mediated specific histamine release with these separated cells. On the other hand, BA312, a monoclonal antibody of the present invention gave an excellent ratio of 7.5%.

TABLE 3

| Monoclonal antibody | CD9 | CD11b | BA20 | BA312 |
|---|---|---|---|---|
| Non-Spec./Spec. (%) | 46.9 | 39.7 | 22.0 | 7.5 |
| SD | 17.6 | 28.5 | 15.1 | 5.3 |

Non-Spec./Spec.: Ratio of amount of histamine released by nonspecific reaction to that of histamine released by IgE-mediated specific reaction
SD: Standard deviation These results demonstrate that the cells separated with magnetic beads having BA20 or BA312 immobilized thereon showed a high basophil capturing rate, good IgE-mediated specific histamine release and most suppressed nonspecific histamine release. The magnetic beads having BA312 immobilized thereon, in particular, were most suitable for basophil separation from human blood and the cells thus separated were most suitable for testing of histamine release from the separated cells according to the present invention.

2. Histamine Release Test with Whole Blood and Separated Cells

Using one blood sample from a normal volunteer, whole blood and separated cells were compared as to histamine release.

In the whole blood method, a 10 ml blood sample was taken in a heparinized blood sampling tube. This blood was dispensed to test tubes at 100 µl per test tube, and 400 µl of histamine release buffer or a 50000, 5000, 500, 50 or 5 ng/ml suspension of monoclonal anti-human IgE antibody (HE-69B) in histamine release buffer was added to each tube, followed by stirring to give a sample (the final concentrations of monoclonal anti-human IgE antibodies were 40000, 4000, 400, 40 and 4 ng/ml, respectively). The total amount of histamine was determined using the sample after 3 cycles of freeze-thawing in the histamine buffer. The IgE-mediated specific histamine release reaction was carried out by reacting a sample with monoclonal anti-human IgE antibody at 37° C. for 1 hour. The nonspecific histamine release reaction was carried out by incubating a sample in the histamine release buffer at 37° C. for 1 hour. After completion of the reaction, the reaction mixture was stirred and then centrifuged at 1500 rpm for 5 minutes, and 300 µl of the supernatant was obtained and assayed for the amount of released histamine by a histamine assay system with HPLC (manufactured by Shimadzu Corporation).

In the separated cell method, cell separation and testing of histamine release from the separated cells were conducted in the same manner as in Example 4 above. Using 40000, 4000, 400, 40 and 4 ng/ml suspensions of monoclonal anti-human IgE antibody (HE-69B) in histamine release buffer, histamine release rate was determined. The specific histamine release rate can be calculated using the following equation:

Ratio of specific histamine release (%) =

$$\frac{\begin{array}{c}\text{Amount of histamine}\\\text{released by}\\\text{IgE specific reaction}\end{array} - \begin{array}{c}\text{Amount of histamine}\\\text{released by}\\\text{nonspecific reaction}\end{array}}{\begin{array}{c}\text{Total amount of}\\\text{histamine}\end{array} - \begin{array}{c}\text{Amount of histamine}\\\text{released by}\\\text{nonspecific reaction}\end{array}} \times 100$$

Figure 2:
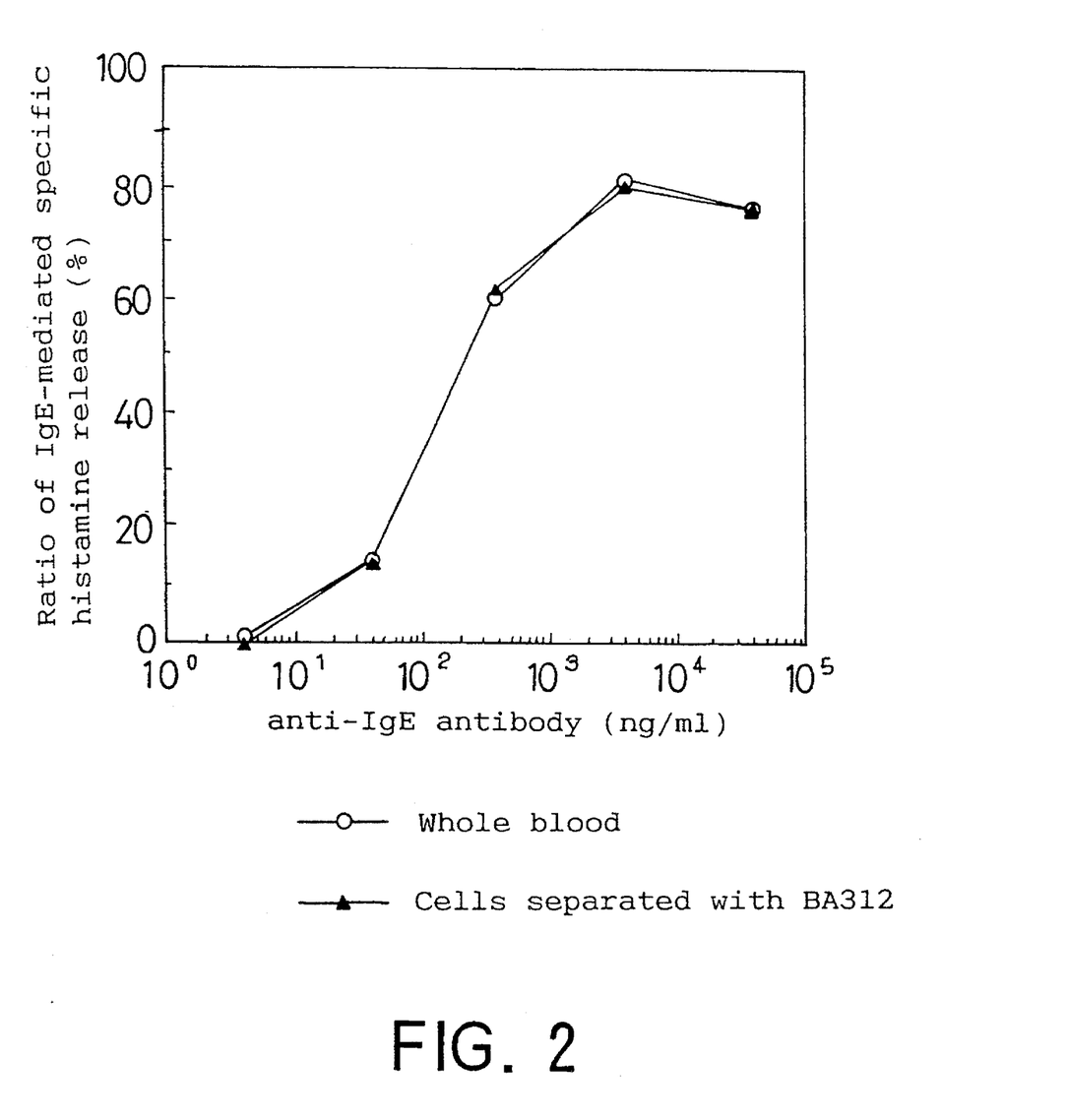
FIG. 2 is a graph showing a curve of anti-human IgE antibody concentration-dependent histamine release reaction using whole blood or the cells separated with the magnetic beads having antibody BA312 immobilized thereon.

As shown in FIG. 2, the whole blood method and the separated cell method gave comparable results for specific histamine release rate. This demonstrates that the cells separated using the monoclonal antibody of the present invention retain their histamine release capability naturally observed in the blood.

3. Histamine Release Test from Separated Cells with Clinical Blood Samples

For two blood samples from pediatric patients with atopic dermatitis caused by egg white, cells were separated and tested for histamine release in the same manner as in Example 4 above, using BA312-immobilized magnetic beads prepared by the method of Example 3 above. The egg white allergen used in the test was adjusted to concentrations of 4000, 400, 40, 4 and 0.4 ng/ml with the histamine release buffer, and the ratio of IgE-mediated specific histamine release was calculated using the equation as described above.

Figure 3:
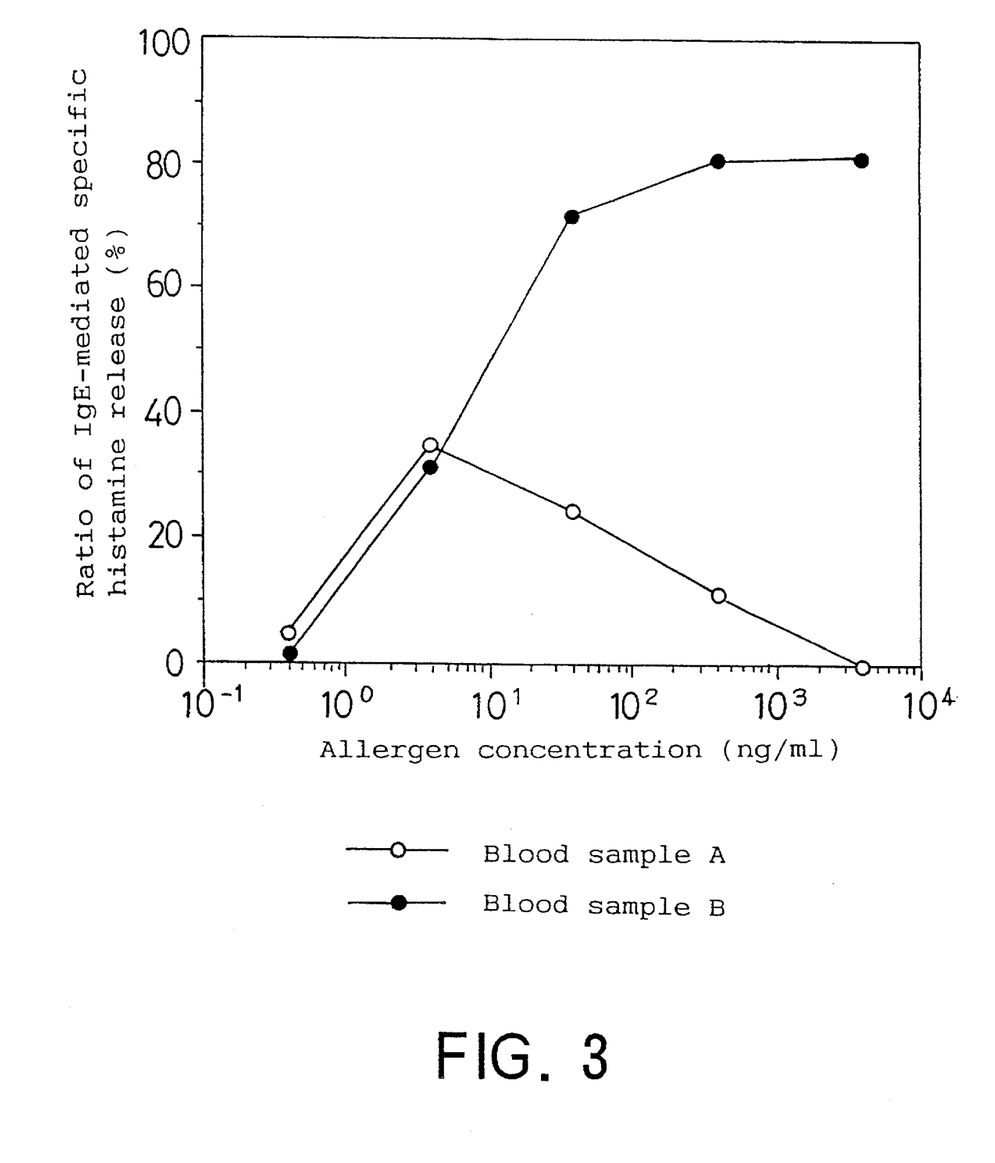
FIG. 3 is a graph showing a curve of egg white allergen concentration-dependent histamine release reaction using the cells separated from the blood of pediatric patients with atopic dermatitis with the magnetic beads having antibody BA312 immobilized thereon.

As shown in FIG. 3, the ratio of IgE-mediated specific histamine release depended on an egg white allergen concentration. Also, a bell-shaped concentration dependency curve was obtained in some cases, in which the histamine release rate decreased as the allergen concentration increased above a given level.

4. Determination of Histamine Concentration by Radioimmunoassay (RIA)

Cells were separated and tested for histamine release in the same manner as in Example 4 above, using BA312-immobilized magnetic beads prepared by the method of Example 3 above.

Figure 4:
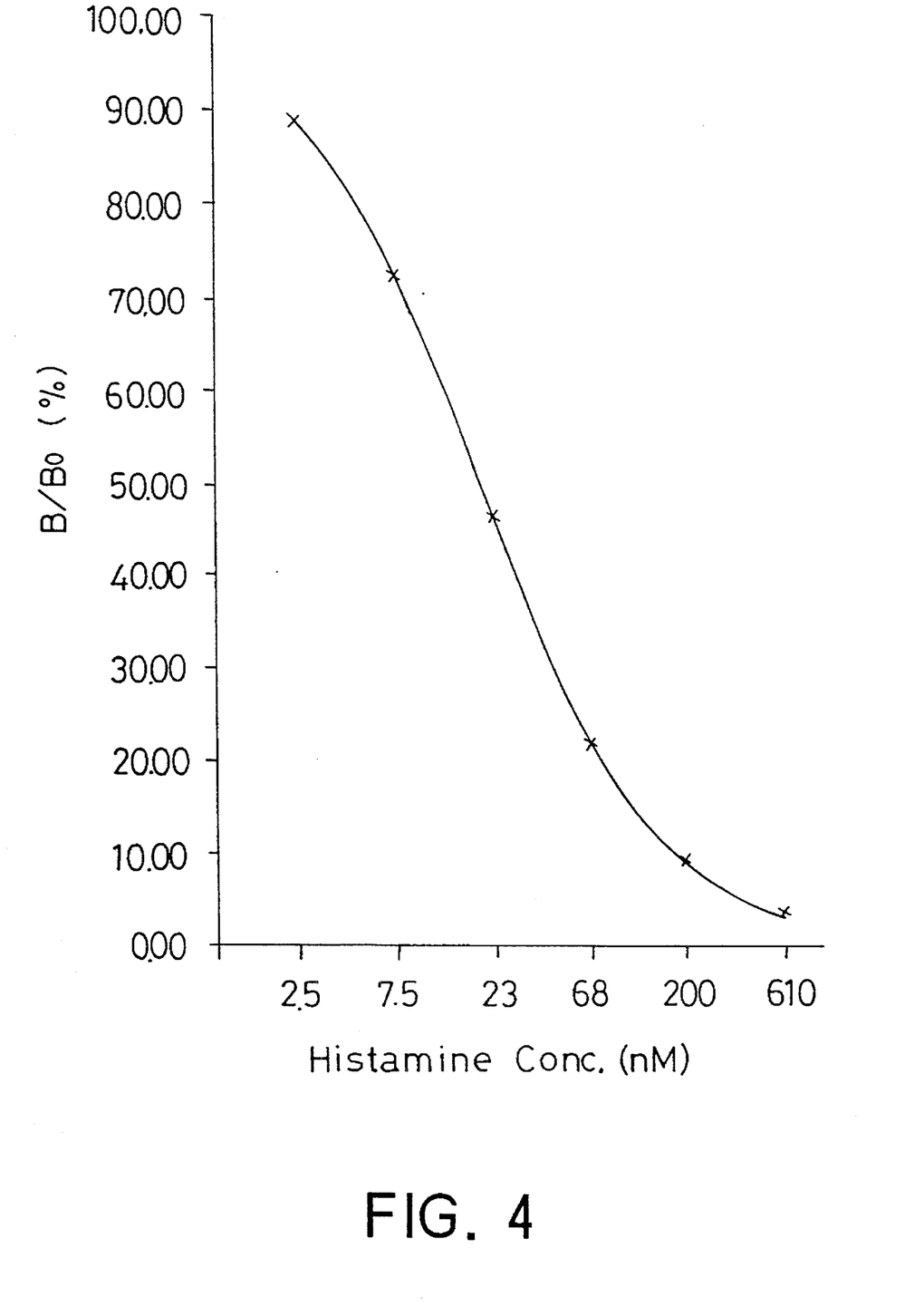
FIG. 4 is a graph showing a standard curve of histamine concentration obtained by RIA. $B/B_0$ means percentage level of labeled analyte bound.

With the sample containing released histamine, the concentration of histamine was determined by radioimmunoassay (RIA). Specifically, 100 µl of a sample containing released histamine or 100 µl of a standard histamine solution was placed in a test tube, respectively. To each test tube, 100 µl of $^{125}$I-labeled histamine solution (10KBq/ml), which was prepared with 50 mM phosphate buffered saline (pH 7.0) containing 0.3% human serum albumin and 0.1% sodium azide (assay buffer), and 100 µl of anti-histamine antibody solution prepared by the assay buffered were added and allowed to react for 2 hours at 4° C. To the reaction mixture, 100 µl of 2.5% bovine γ-globulin solution prepared with 50 mM phosphate buffered saline (pH 7.0) containing 0.1% sodium azide (50 mM PBS) and 500 µl of 25% polyethyleneglycol solution (PEG No. 6000) prepared with 50 mM PBS were added and allowed to react for 10 minutes at 4° C. After the completion of the reaction, it was centrifuged at 1800×g for 20 minutes at 4° C., and the radioactivity of the sediment was determined. FIG. 4 shows the standard curve of histamine concentration obtained by RIA.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for detecting chemical mediator release from basophils, comprising:
   1) separating leukocytes including basophils from a humoral fluid by contacting said fluid with a reagent comprising a monoclonal antibody immobilized on a solid carrier, wherein the monoclonal antibody has the following properties:
      (a) specifically binds to an antigen on the surface of basophils,
      (b) retains its specific binding reactivity with leukocytes including basophils even after immobilization onto the solid carrier, so as to provide, upon specific binding to basophils, immobilized basophils in a physiological condition sufficient for a chemical mediator release test,
      (c) does not inhibit IgE-mediated specific histamine release from said immobilized basophils,
      (d) does not induce nonspecific histamine release from said basophils,
      (e) is of an IgG or IgM isotype, and
      (f) specifically binds to said antigen through the Fab portion of the antibody;
   2) contacting the separated leukocytes including basophils with an allergen or anti-IgE antibody to release a chemical mediator; and
   3) detecting the chemical mediator thus released from said leukocytes including basophils.

2. A method for determining amount of release of a chemical mediator from basophils, comprising:
   1) separating leukocytes including basophils from a humoral fluid by contacting said fluid with a reagent comprising a monoclonal antibody immobilized on a solid carrier, wherein the monoclonal antibody has the following properties:
      (a) specifically binds to an antigen on the surface of basophils,
      (b) retains its specific binding reactivity with leukocytes including basophils even after immobilization onto the solid carrier, so as to provide, upon specific binding to basophils, immobilized basophils in a physiological condition sufficient for a chemical mediator release test,
      (c) does not inhibit IgE-mediated specific histamine release from said immobilized basophils,
      (d) does not induce nonspecific histamine release from said basophils,
      (e) is of an IgG or IgM isotype, and
      (f) specifically binds to said antigen through the Fab portion of the antibody;
   2) contacting the separated leukocytes including basophils with an allergen or anti-IgE antibody to release a chemical mediator; and
   3) determining the amount of the chemical mediator thus released from said leukocytes including basophils.

3. The method of claim 1 or 2, wherein said humoral fluid is selected from the group consisting of blood, a nasal secretion, tears and saliva.

4. The method of claim 1 or 2, wherein said monoclonal antibody is selected from the group consisting of monoclonal antibodies BA101, BA20, BA135 and BA312, produced by hybridoma FERM BP-4004, FERM BP-4005, FERM BP-4006 and FERM BP-4007, respectively.

5. The method of claim 1 or 2, wherein said solid carrier is selected from the group consisting of glass particles, synthetic resin particles, glass spheres, synthetic resin spheres, glass tubes, synthetic resin tubes, glass plates, synthetic resin plates, magnetic particles and magnetic beads.

6. The method of claim 4, wherein said solid carrier is magnetic beads.

7. The method of claim 1 or 2, wherein said chemical mediator is selected from the group consisting of histamine, a leukotriene, and platelet activating factor.

8. The method of claim 1 or 2, wherein step (2) is performed by contacting said leukocytes including basophils with an allergen selected from the group consisting of house dust, pollen, a dietary allergen and a chemical substance.

9. A method for determining the amount of chemical mediator release from leukocytes including basophils, comprising:

(1) providing a solid carrier-immobilized monoclonal antibody which is selected from the group consisting of monoclonal antibodies BA101, BA20, BA135 and BA312, produced by hybridoma FERM BP-4004, FERM BP-4005, FERM BP-4006 and FERM BP-4007, respectively;

(2) reacting the solid carrier-immobilized monoclonal antibody of step (1) with a humoral fluid to obtain immobilized leukocytes including basophils;

(3) separating said immobilized leukocytes including basophils from said humoral fluid;

(4) reacting the leukocytes including basophils separated in step (3) with an allergen or anti-IgE antibody to release a chemical mediator from said leukocytes including basophils; and (5) determining the amount of the chemical mediator released in step (4) from said leukocytes including basophils.

* * * * *